United States Patent
Conley et al.

(10) Patent No.: US 9,480,475 B2
(45) Date of Patent: Nov. 1, 2016

(54) BONE PLATE SUTURE ANCHOR

(71) Applicant: DEPUY SYNTHES PRODUCTS, INC., Raynham, MA (US)

(72) Inventors: Jordan P. Conley, West Chester, PA (US); Abhishek P. Modi, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 637 days.

(21) Appl. No.: 13/829,171

(22) Filed: Mar. 14, 2013

(65) Prior Publication Data

US 2014/0052176 A1    Feb. 20, 2014

Related U.S. Application Data

(60) Provisional application No. 61/683,382, filed on Aug. 15, 2012.

(51) Int. Cl.
*A61B 17/04* (2006.01)
*A61B 17/80* (2006.01)
*A61B 17/064* (2006.01)

(52) U.S. Cl.
CPC ....... *A61B 17/0642* (2013.01); *A61B 17/0401* (2013.01); *A61B 17/80* (2013.01);
(Continued)

(58) Field of Classification Search
CPC .............. A61B 17/0401; A61B 17/80; A61B 2017/0408; A61B 2017/0409; A61B 2017/0412; A61B 2017/0427; A61B 2017/0437; A61B 2017/0438; A61B 2017/044; A61B 2017/0445; A61B 2017/0446; A61B 2017/0448; A61B 2017/0456; A61B 2017/0458; A61F 2/0811; A61F 2002/0817; A61F 2002/0847; A61F 2002/0864; A61F 2002/0888
See application file for complete search history.

(56) References Cited

U.S. PATENT DOCUMENTS

| 362,183 A | 5/1887 | Runyon |
|---|---|---|
| 1,102,485 A | 7/1914 | Ehleet |

(Continued)

FOREIGN PATENT DOCUMENTS

| DE | 10 2010 042 930 | 4/2012 |
|---|---|---|
| EP | 0 594 002 | 4/1994 |

(Continued)

OTHER PUBLICATIONS

International Search Report and Written Opinion (PCT/US2008/077997); Nov. 28, 2008.

(Continued)

*Primary Examiner* — Ryan J Severson
(74) *Attorney, Agent, or Firm* — Dunlap Codding, P.C.

(57) ABSTRACT

A suture anchor insert comprising a body configured to be inserted into a hole in a bone plate. The body has a proximal end, a distal end, a length extending between the proximal and distal ends and substantially corresponding to a thickness of a bone plate, a sidewall, at least one plate engaging member extending outwardly from the sidewall to secure the body to the bone plate, a recess defined by the sidewall, and a transverse edge formed on the sidewall. A crossbar extends inwardly from the sidewall across the recess such that a free end of the crossbar is normally disposed distally of the transverse edge. The crossbar is flexible such that when a distally directed force is applied, the free end of the crossbar is positionable in the recess. The free end of the crossbar is engageable with the transverse edge to limit proximal motion of the crossbar.

8 Claims, 6 Drawing Sheets

(52) U.S. Cl.
CPC .. *A61B2017/0403* (2013.01); *A61B 2017/044* (2013.01); *A61B 2017/0438* (2013.01); *A61B 2017/0448* (2013.01); *A61B 2017/0458* (2013.01)

(56) References Cited

U.S. PATENT DOCUMENTS

| | | | |
|---|---|---|---|
| 4,590,928 A * | 5/1986 | Hunt | A61B 17/686 606/327 |
| 5,209,756 A | 5/1993 | Seedhom et al. | |
| 5,217,486 A | 6/1993 | Rice et al. | |
| 5,222,961 A | 6/1993 | Nakao et al. | |
| 5,441,502 A | 8/1995 | Bartlett | |
| 5,507,754 A | 4/1996 | Green et al. | |
| 5,527,343 A | 6/1996 | Bonutti | |
| 5,681,352 A | 10/1997 | Clancy, III et al. | |
| 5,702,397 A | 12/1997 | Goble et al. | |
| 5,718,717 A | 2/1998 | Bonutti | |
| 5,782,866 A | 7/1998 | Wenstrom, Jr. | |
| 5,842,478 A | 12/1998 | Benderev et al. | |
| 5,891,168 A | 4/1999 | Thal | |
| 5,906,624 A | 5/1999 | Wenstrom, Jr. | |
| 5,957,953 A | 9/1999 | DiPoto et al. | |
| 5,980,558 A | 11/1999 | Wiley | |
| 5,980,559 A | 11/1999 | Bonutti | |
| 6,024,758 A | 2/2000 | Thal | |
| 6,077,292 A | 6/2000 | Bonutti | |
| 6,336,928 B1 | 1/2002 | Guerin et al. | |
| 6,500,195 B2 | 12/2002 | Bonutti | |
| 6,652,563 B2 | 11/2003 | Dreyfuss | |
| 6,702,821 B2 | 3/2004 | Bonutti | |
| 6,733,506 B1 | 5/2004 | McDevitt et al. | |
| 6,773,437 B2 | 8/2004 | Ogilvie et al. | |
| 6,855,157 B2 | 2/2005 | Foerster et al. | |
| 7,087,073 B2 | 8/2006 | Bonutti | |
| 7,217,279 B2 | 5/2007 | Reese | |
| 7,322,978 B2 | 1/2008 | West, Jr. | |
| 7,481,825 B2 | 1/2009 | Bonutti | |
| 7,566,339 B2 | 7/2009 | Fallin et al. | |
| 7,585,311 B2 | 9/2009 | Green et al. | |
| 7,806,896 B1 | 10/2010 | Bonutti | |
| 7,914,574 B2 | 3/2011 | Schmid et al. | |
| 7,959,650 B2 | 6/2011 | Kaiser et al. | |
| 8,088,163 B1 | 1/2012 | Kleiner | |
| 8,114,081 B2 | 2/2012 | Kohut et al. | |
| 8,118,835 B2 | 2/2012 | Weisel et al. | |
| 8,118,836 B2 | 2/2012 | Denham et al. | |
| 8,267,973 B2 | 9/2012 | Humphrey | |
| 2002/0052629 A1 | 5/2002 | Morgan et al. | |
| 2003/0120309 A1 | 6/2003 | Colleran et al. | |
| 2004/0010287 A1 | 1/2004 | Bonutti | |
| 2004/0098050 A1 | 5/2004 | Foerster et al. | |
| 2004/0133239 A1 | 7/2004 | Singhatat | |
| 2004/0153153 A1 | 8/2004 | Elson et al. | |
| 2005/0149027 A1 | 7/2005 | Campbell et al. | |
| 2005/0222618 A1 | 10/2005 | Dreyfuss et al. | |
| 2005/0283158 A1 | 12/2005 | West, Jr. | |
| 2006/0004364 A1 | 1/2006 | Green et al. | |
| 2006/0015108 A1 | 1/2006 | Bonutti | |
| 2006/0106423 A1 | 5/2006 | Weisel et al. | |
| 2006/0161157 A1 | 5/2006 | Mosca et al. | |
| 2006/0229620 A1 | 10/2006 | Rothman et al. | |
| 2006/0259076 A1 | 11/2006 | Burkhart et al. | |
| 2006/0282081 A1 | 12/2006 | Fanton et al. | |
| 2007/0005068 A1 | 1/2007 | Sklar | |
| 2007/0073299 A1 | 3/2007 | Dreyfuss et al. | |
| 2007/0093835 A1 | 4/2007 | Orbay et al. | |
| 2007/0135843 A1 | 6/2007 | Burkhart | |
| 2007/0270849 A1 | 11/2007 | Orbay et al. | |
| 2007/0270853 A1 | 11/2007 | Leung | |
| 2008/0132944 A1 | 6/2008 | Kress | |
| 2008/0188893 A1 | 8/2008 | Selvitelli et al. | |
| 2009/0082807 A1 | 3/2009 | Miller et al. | |
| 2009/0088798 A1 | 4/2009 | Snyder et al. | |
| 2009/0088808 A1 | 4/2009 | Lindemann et al. | |
| 2009/0118776 A1 | 5/2009 | Kelsch et al. | |
| 2009/0187218 A1 | 7/2009 | Schaffhausen | |
| 2009/0216270 A1 | 8/2009 | Humphrey | |
| 2009/0264936 A1 | 10/2009 | Gonzalez-Hernandez et al. | |
| 2009/0292313 A1 | 11/2009 | Anspach, III et al. | |
| 2010/0094337 A1 | 4/2010 | Maiorino | |
| 2010/0121355 A1 | 5/2010 | Gittings et al. | |
| 2010/0292732 A1 | 11/2010 | Hirotsuka et al. | |
| 2011/0022083 A1 | 1/2011 | DiMatteo et al. | |
| 2011/0022084 A1 | 1/2011 | Sengun et al. | |
| 2011/0054523 A1 | 3/2011 | O'Neill et al. | |
| 2011/0152928 A1 | 6/2011 | Colleran et al. | |
| 2011/0152929 A1 | 6/2011 | McDevitt et al. | |
| 2011/0160768 A1 | 6/2011 | Stone et al. | |
| 2011/0208239 A1 | 8/2011 | Stone et al. | |
| 2011/0264141 A1 | 10/2011 | Denham et al. | |
| 2011/0313453 A1 | 12/2011 | Krumme et al. | |
| 2012/0053622 A1 | 3/2012 | Schulman | |
| 2012/0053630 A1 | 3/2012 | Denham et al. | |
| 2012/0130422 A1 | 5/2012 | Hootstein | |
| 2012/0158051 A1 | 6/2012 | Foerster | |
| 2012/0165866 A1 | 6/2012 | Kaiser et al. | |
| 2012/0172930 A1 | 7/2012 | Gagliano | |
| 2012/0180291 A1 | 7/2012 | Oren et al. | |
| 2012/0191140 A1 | 7/2012 | Bonutti | |
| 2012/0209325 A1 | 8/2012 | Gagliano et al. | |

FOREIGN PATENT DOCUMENTS

| | | |
|---|---|---|
| EP | 1 011 472 | 6/2000 |
| EP | 1 764 053 | 3/2007 |
| FR | 2 731 610 | 9/1996 |
| JP | 2007-083047 | 4/2007 |
| WO | 94/15535 | 7/1994 |
| WO | 2006/037131 | 4/2006 |
| WO | 2007/078281 | 7/2007 |
| WO | 2010/121234 | 10/2010 |
| WO | 2011/085272 | 7/2011 |
| WO | 2012/024446 | 2/2012 |
| WO | 2012/135141 | 10/2012 |

OTHER PUBLICATIONS

International Search Report and Written Opinion (PCT/US2011/048149); Apr. 23, 2012.
International Search Report and Written Opinion (PCT/US2012/030608); Sep. 25, 2012.
Search Report, State Intellectual Property Office of the People Republic of China (CN201180040063.4); Dec. 2014.
Extended European Search Report (EP 08833893.4); Feb. 6, 2015.
International Search Report and Written Opinion (PCT/US2013/055060); Feb. 19, 2014.
Supplementary European Search Report (EP 12763219.8); Feb. 27, 2015.

* cited by examiner

BONE PLATE SUTURE ANCHOR

INCORPORATION BY REFERENCE

The entirety of U.S. provisional application Ser. No. 61/683,382 filed on Aug. 15, 2012, is hereby expressly incorporated herein by reference.

BACKGROUND

Bone fractures may take many forms: complete, incomplete, simple, comminuted, closed, or open. Fractures may also be associated with separation of connections between soft tissue and bone. Fractures, with and without soft tissue separation, often require stabilization to promote faster healing and unimpaired function. Stabilization may return function and mobility for the injured area earlier than treatment without stabilization. Fracture fixation and stabilization procedures are generally of two types, internal or external. External fixation methods may include slings, splints, or casts. Internal fixation methods may employ wires, pins and screws, bone plates, and intramedullary nails or rods.

Fractures treated with bone plates may be treated by exposing the fracture site and reducing the bone fracture, then placing a plate onto the bone to secure the fracture for healing in the reduced position. In reducing the bone, the fracture and surrounding bone are realigned and positioned in the original bone position or a similar stable position. Bone plates may be used in flexible fracture fixation or rigid fixation. Flexible fixation occurs where the fracture fragments displace in relation to each other when a load is applied across the fracture site. Rigid fixation techniques employ plates and screws in order to limit displacement of fracture fragments in relation to each other.

Where fractures are associated with the separation of bone and soft tissue, such as ligaments or tendons, the separation may take the form of a separation of the soft tissue at the osseous junction or a fracture at a tuberosity. Tuberosities, the bone site for attachment between tendon and bone, may be displaced in a fracture. Ligaments and tendons may be detached from the bone at the fibro-osseous junction, which is the connection between the soft tissue and bone. Where a fracture is associated with a tendon or ligament separation, fixation of the fracture may require anchoring of the tendon or ligament to the bone.

Suture anchors are commonly used to anchor soft tissue to bone. Suture anchors are generally implanted into the bone so as to secure one or more sutures extending from a body used to secure the soft tissue by holding the tissue in position to the bone. Bone plates have also been used as a securing element for sutures. The sutures have been secured to the plate by threading the sutures through holes in the plate before the plate is secured to the bone. The use of bone plates to anchor sutures in this manner often limits the suture attachment locations available to a surgeon, particularly after the plate has been attached to the bone.

DETAILED DESCRIPTION OF EXEMPLARY EMBODIMENTS

Figure 1:
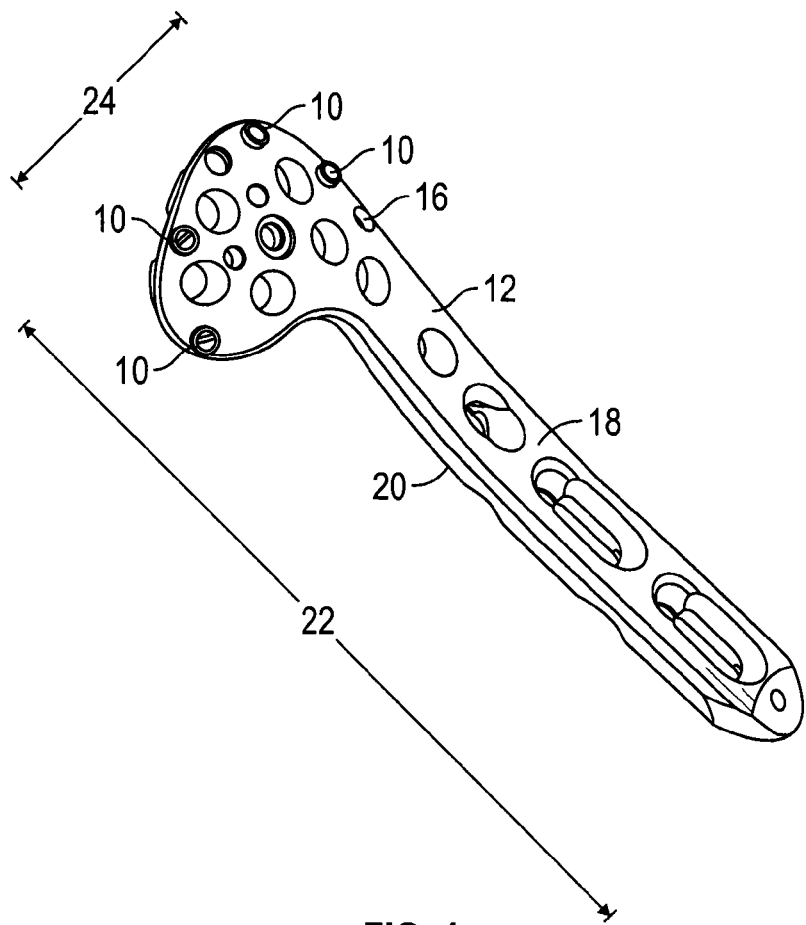
FIG. 1 is a perspective view of a bone plate with a suture anchor insert constructed in accordance with the inventive concepts disclosed herein.
Figure 2:
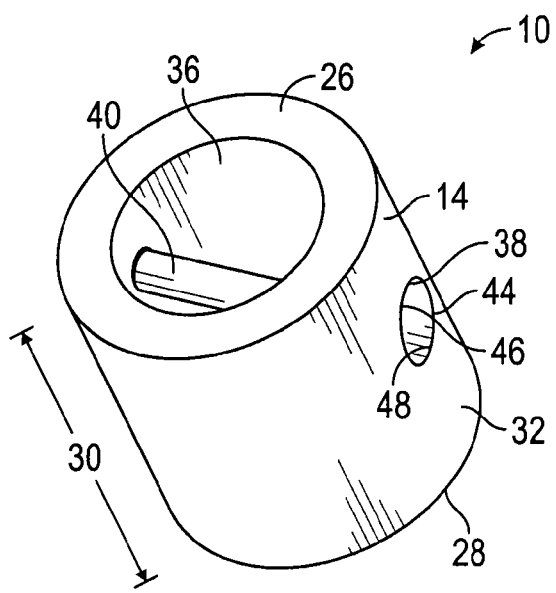
FIG. 2 is a perspective view of the suture anchor insert constructed in accordance with the inventive concepts disclosed herein.
Figure 3:
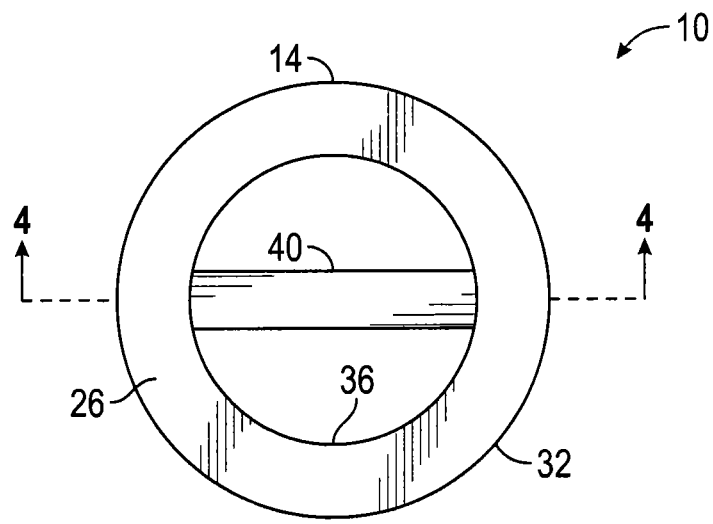
FIG. 3 is a top plan view of the suture anchor insert of FIG. 2.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

Referring to the drawings, and more particularly to FIG. 1, a plurality of suture anchor inserts 10 constructed in accordance with the inventive concepts disclosed herein are shown inserted into a bone plate 12. The plate 12 has an upper surface 18, a lower surface 20, a length 22, and a width 24. The plate 12 has a plurality of holes 16 formed therein extending through the plate 12 from the upper surface 18 to the lower surface 20. The plurality of holes 16 may comprise threaded holes, non-threaded holes, partially threaded holes, tapered holes, and straight holes, for example. The bone plate 12, shown in FIG. 1, is an example of the bone plate 12, however, it will be appreciated by one skilled in the art that the bone plate 12 may be provided in varying forms while being in accordance with the inventive concepts disclosed herein. For example, the bone plate 12 may be substantially rectangular or circular in shape. The bone plate 12 may employ a "T", "Y", or "H" shape. The bone plate 12 may be provided with holes 16 disposed in a single line, parallel lines, offset from one another, or staggered about the bone plate 12. The bone plate 12 may also have sections disposed at an angle to a plane of a remaining section of the bone plate 12.

Figure 4A:
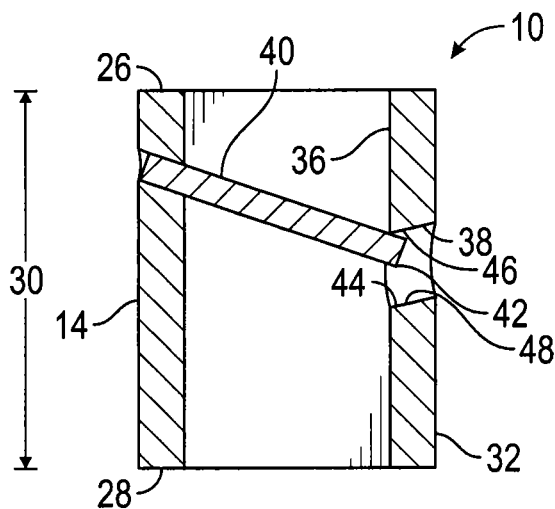
FIG. 4A is a sectional view taken along line 4-4 of FIG. 3 illustrating a crossbar in an unflexed condition.
Figure 4B:
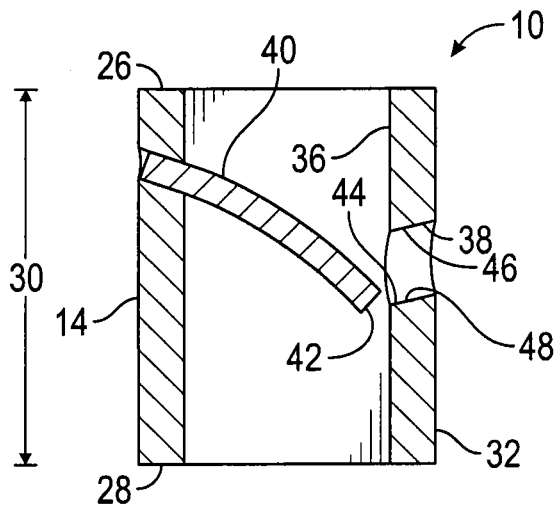
FIG. 4B is a sectional view of the suture anchor insert of FIG. 4A illustrating the crossbar in a flexed condition.
Figure 5:
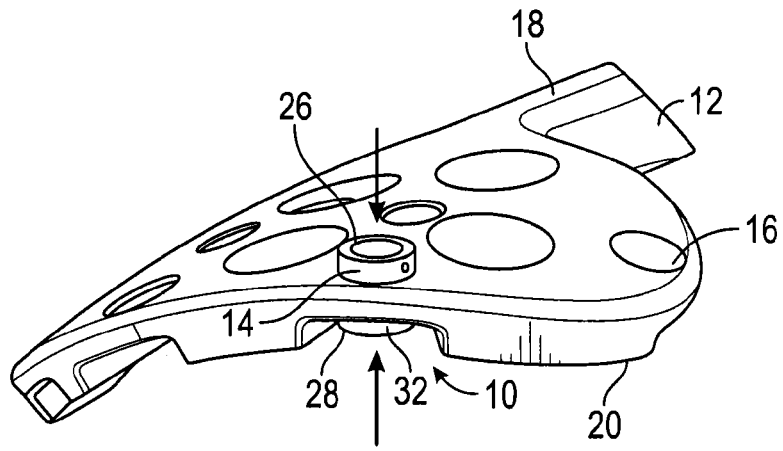
FIG. 5 is a perspective view of the suture anchor insert of FIG. 2 shown being installed into a bone plate.
Figure 6:
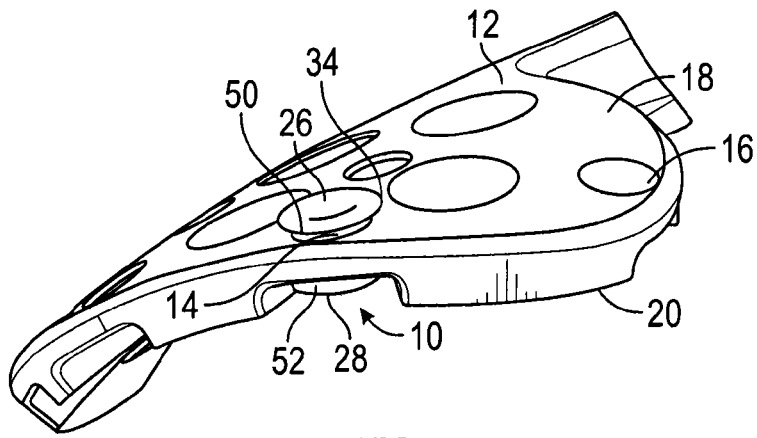
FIG. 6 is a perspective view of the suture anchor insert of FIG. 2 shown installed in the bone plate.

Referring now to FIGS. 2-6, the suture anchor insert 10 has a body 14 configured to be slidably inserted into one of the holes 16 of the bone plate 12. The body 14 has a proximal end 26, a distal end 28, a length 30 extending between the proximal end 26 and the distal end 28 substantially corresponding to a thickness of the plate 12, and a sidewall 32 extending between the proximal end 26 and the distal end 28. The sidewall 32 is provided with at least one plate engaging member 34 (FIG. 6). The sidewall 32 defines a recess 36 within the body 14 of the suture anchor insert 10. The sidewall 32 is further provided with a transverse edge 38. Opposite the transverse edge 38, the sidewall 32 is provided with a crossbar 40.

The crossbar 40 extends inwardly therefrom across the recess 36 such that a free end 42 of the crossbar 40 is normally disposed distally of the transverse edge 38 (FIG. 4A). The crossbar 40 is flexible such that when a distally directed force is applied to the crossbar 40, the free end 42 of the crossbar 40 is positioned in the recess 36 (FIG. 4B) and when a proximally directed force is applied to the crossbar 40 such as by a suture which is looped over the crossbar 40, the free end 42 of the crossbar 40 engages with the transverse edge 38 to limit proximal motion of the crossbar 40.

The sidewall 32 of the body 14 may be provided with a crossbar window 44 which is in communication with the recess 36. The crossbar window 44 has a proximal side 46 and a distal side 48 where the proximal side 46 of the crossbar window 44 defines the transverse edge 38. The crossbar 40 extends across the recess 36 such that the free end 42 of the crossbar 40 is normally disposed in the crossbar window 44.

In one embodiment, the plate engaging member 34 is formed after insertion of the suture anchor insert 10 into the hole 16 of the plate 12. FIG. 5 illustrates, in this embodiment, the initial length 22 of the suture anchor insert 10 is greater than the thickness of the plate 12, such that when initially inserted into the plate 12, the proximal end 26 and the distal end 28 extend past the upper surface 18 and the lower surface 20 of the plate 12, respectively.

Figure 7:
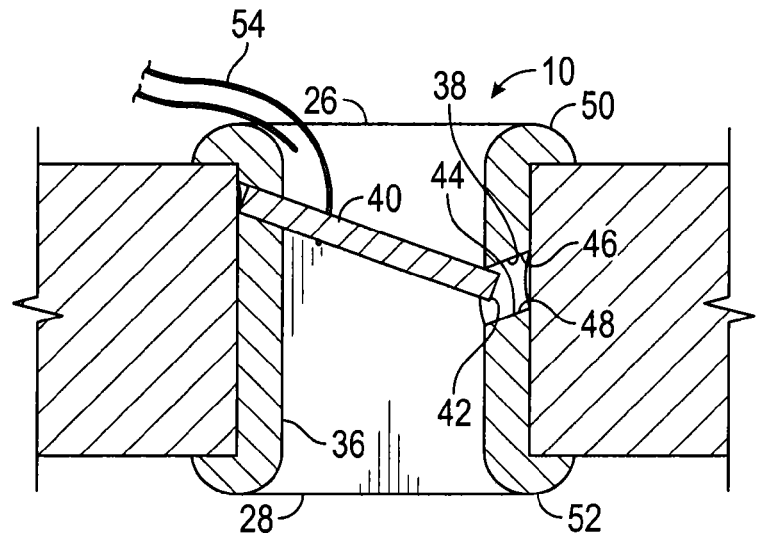
FIG. 7 is a sectional view of the suture anchor insert of FIG. 2 shown with a suture captured by the suture anchor insert.

As shown in FIGS. 6 and 7, once the suture anchor insert 10 is inserted into the hole 16 with the proximal end 26 and the distal end 28 of the suture anchor insert 10 extending past the upper surface 18 and the lower surface 20, respectively, the proximal end 26 and distal end 28 may be deformed. The proximal end 26 may be deformed in a distal direction toward the upper surface 18 of the plate 12 until the proximal end 26 contacts the upper surface 18, forming a first lip 50 extending outwardly at the proximal end 26 and engageable with the upper surface 18 of the plate 12. Similarly, the distal end 28 may be deformed in a proximal direction toward the lower surface 20 of the plate 12 until the distal end 28 contacts the lower surface 20, forming a second lip 52 extending outwardly at the distal end 28 and engageable with the lower surface 20 of the plate 12. The proximal end 26 and distal end 28 may be deformed, for example, by compressing, rolling, splitting, or capping the proximal end 26 and distal end 28.

One or more sutures 54 (FIG. 7) may be attached to the suture anchor insert 10 after the suture anchor insert 10 has been inserted into the plate 12 and the first lip 50 and the second lip 52 have been formed on the upper surface 18 and the lower surface 20, respectively, securing the suture anchor insert 10 in place in the hole 16. If desired, the one or more sutures 54 may be attached prior to insertion of the suture anchor insert 10 into the plate 12. The one or more sutures 54 may be attached to suture anchor insert 10 in any suitable fashion. By way of example, the one or more sutures 54 may be positioned about the crossbar 40 with a suture threader which is disclosed in U.S. Publication No. 2009/0088798, which is hereby expressly incorporated herein by reference.

The suture anchor insert 10 may be placed in selected locations on the plate 12 by inserting the suture anchor insert 10 into a selected one of the plurality of holes 16 of the bone plate 12. The plurality of positions available for insertion of the suture anchor insert 10 enable placement of one or more sutures 54 according to the needs of the surgeon at the time of placement of the plate 12, the suture anchor insert 10, and the sutures 54. Maintaining the variability of the suture anchor insert 10, the suture anchor insert 10 may be provided as a kit including the plate 12 and at least one suture anchor insert 10.

Figure 8:
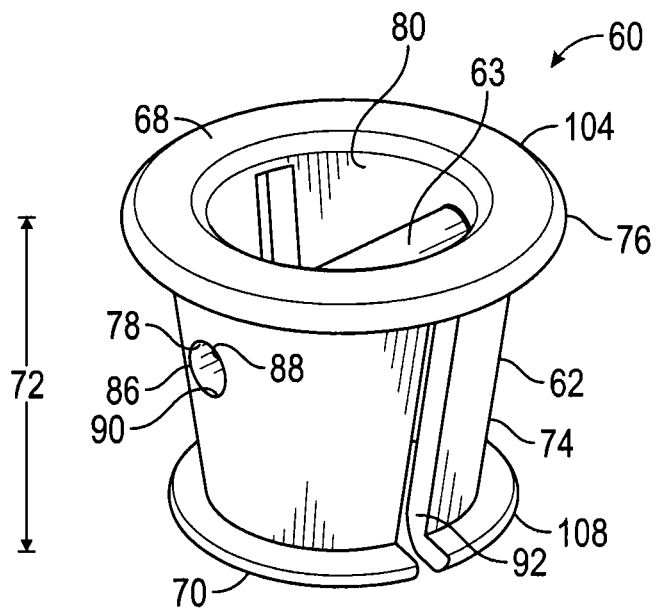
FIG. 8 is a perspective view of another embodiment of a suture anchor insert constructed in accordance with the inventive concepts disclosed herein.
Figure 9:
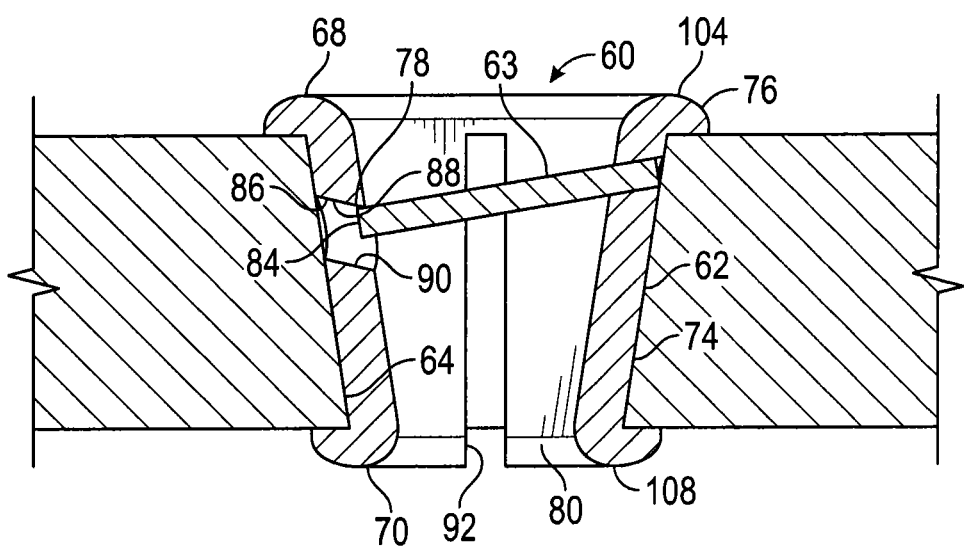
FIG. 9 is a sectional view of the suture anchor insert of FIG. 8 shown inserted into a bone plate.

Referring now to FIGS. 8 and 9, another embodiment of a suture anchor insert 60 constructed in accordance with the inventive concepts disclosed herein is illustrated. The suture anchor insert 60 has a body 62 and a crossbar 63. The body 62 is configured to be slidably inserted into the hole 16 in the bone plate 12. The body 62 has a proximal end 68, a distal end 70, a length 72 extending between the proximal end 68 and the distal end 70 substantially corresponding to a thickness of the plate 12, and a sidewall 74 extending between the proximal end 68 and the distal end 70. The body 62 of the suture anchor insert 60 is distally tapered from the proximal end 68 toward the distal end 70 to engage a hole 64 having a corresponding distal taper, the body 62 conforming to the contour of the hole 64. The sidewall 74 is provided with a plate engaging member 76 extending outwardly therefrom, and a transverse edge 78. The sidewall 74 defines a recess 80 within the body 62 of the suture anchor insert 60.

The crossbar 63 extends inwardly from the sidewall 74 and across the recess 80 such that a free end 84 of the crossbar 63 is normally disposed distally of the transverse edge 78. The crossbar 63 is flexible such that when a distally directed force is applied to the crossbar 63, the free end 84 of the crossbar 63 is positioned in the recess 80 and when a proximally directed force is applied to the crossbar 63, the free end 84 of the crossbar 63 engages with the transverse edge 78 to limit proximal motion of the crossbar 63.

The sidewall 74 may be provided with a crossbar window 86 which is in communication with the recess 80. The crossbar window 86 has a proximal side 88 and a distal side 90 where the proximal side 88 of the crossbar window 86 defines the transverse edge 78. The crossbar 63 extends across the recess 80 such that the free end 84 of the crossbar 63 is normally disposed in the crossbar window 86.

The sidewall 74 is further provided with a pair of slots 92. In one embodiment, the slots 92 are formed in a diametrically opposed relationship to one another and extend from the distal end 70 toward the proximal end 68 of the suture anchor insert 60 to enable compression of the body 62 such that the body 62 is moveable between a compressed position, wherein the suture anchor insert 60 is slidable into the hole 16 of the plate 12, and an expanded position, wherein the suture anchor insert 60 is secured within the hole 16 in the plate 12. When the body 62 of the suture anchor insert 60 is in the compressed position, the crossbar 63 is moveable within the crossbar window 86 without limiting the compression of the body 62. While the sidewall 74 has been shown to include two slots 92, it will be appreciated that the number of slots 92 may vary and the slots 92 may be placed at varying positions and orientations relative to one another to facilitate compression of the body 62.

In one embodiment, the plate engaging members 76 is in the form of a first lip 104 extending outwardly at the proximal end 68 of the sidewall 74 and engageable with the upper surface 18 of the plate 12, and a second lip 108 extending outwardly at the proximal end 68 of the sidewall 74 and engageable with the lower surface 20 of the plate 12. The second lip 108 may be curved at the distal end 70 of the suture anchor insert 60 to facilitate slidably inserting the suture anchor insert 60 into the plate 12.

The suture anchor insert 60 is slidably inserted into the plate 12 by compressing the body 62 near the distal end 70 of the suture anchor insert 60. The suture anchor insert 60 is then positioned at the entrance of the hole 16. Thus positioned, the suture anchor insert 60 is slidably inserted into the hole 16 by a distally directed force exerted on the suture anchor insert 60. Once the second lip 108 slides through the hole 16 and past the lower surface 20, the suture anchor insert 60 reverts to the expanded position, causing the first lip 104 to engage the upper surface 18 of the plate 12 and the second lip 108 to engage the lower surface 20 of the plate 12, thereby securing the suture anchor insert 60 within the hole 16 of the plate 12.

One or more sutures may be attached to the suture anchor insert 60 by disposing the one or more sutures about the crossbar 63. The one or more sutures may be attached to suture anchor insert 60 in any suitable fashion, as previously discussed, such as by use of a suture threader.

The suture anchor insert 60 may be placed in selected locations on the plate 12 by inserting the suture anchor insert 60 into one of the plurality of holes 16 of the plate 12. The plurality of positions available for insertion of the suture anchor insert 60 enable placement of sutures according to the needs of the surgeon at the time of placement of the sutures. Maintaining the variability of the suture anchor insert 60, the suture anchor insert 60 may be provided as a kit including the plate 12 and at least one suture anchor insert 60.

Figure 10:
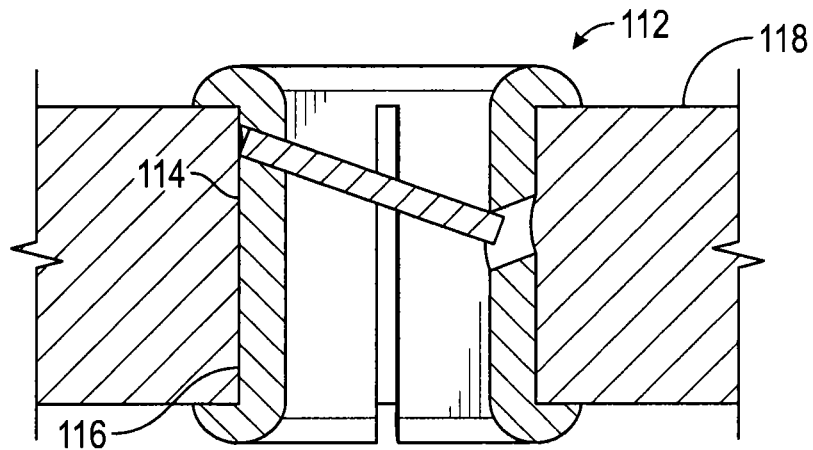
FIG. 10 is a sectional view of another embodiment of a suture anchor insert constructed in accordance with the inventive concepts disclosed herein.

Shown in FIG. 10 is another embodiment of a suture anchor insert 112. The suture anchor insert 112 is substantially similar in construction and function to the suture anchor insert 60, except that suture anchor insert 112 has a body 114 with no distal taper. Thus, the body 114 is inserted into a hole 116 of a plate 118 which has a straight configuration.

Figure 11:
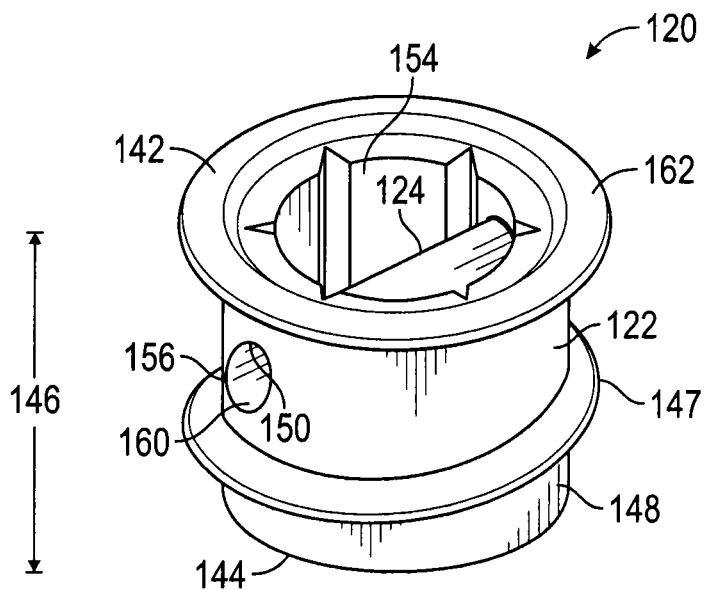
FIG. 11 is a perspective view of another embodiment of a suture anchor insert constructed in accordance with the inventive concepts disclosed herein.
Figure 12:
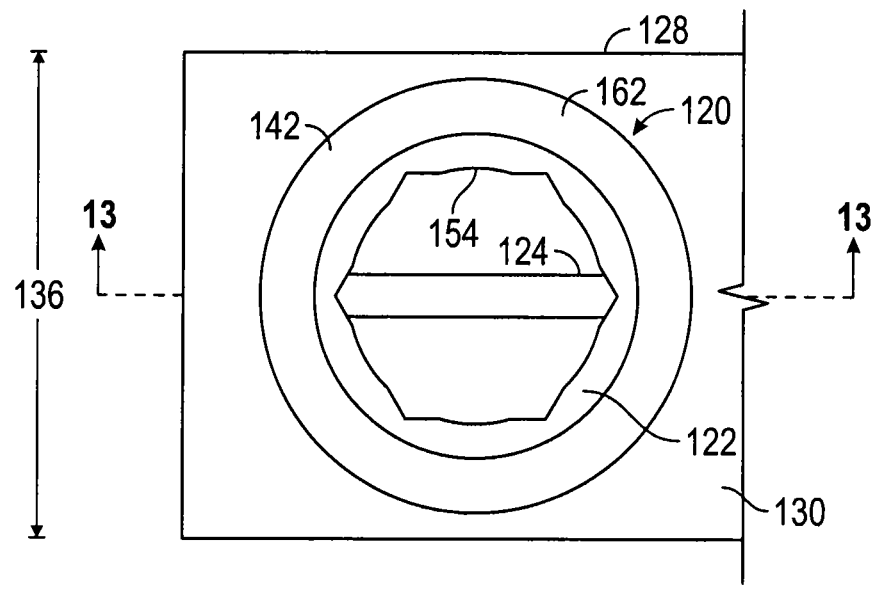
FIG. 12 is a top plan view of the suture anchor insert of FIG. 11 shown inserted into a bone plate.
Figure 13:
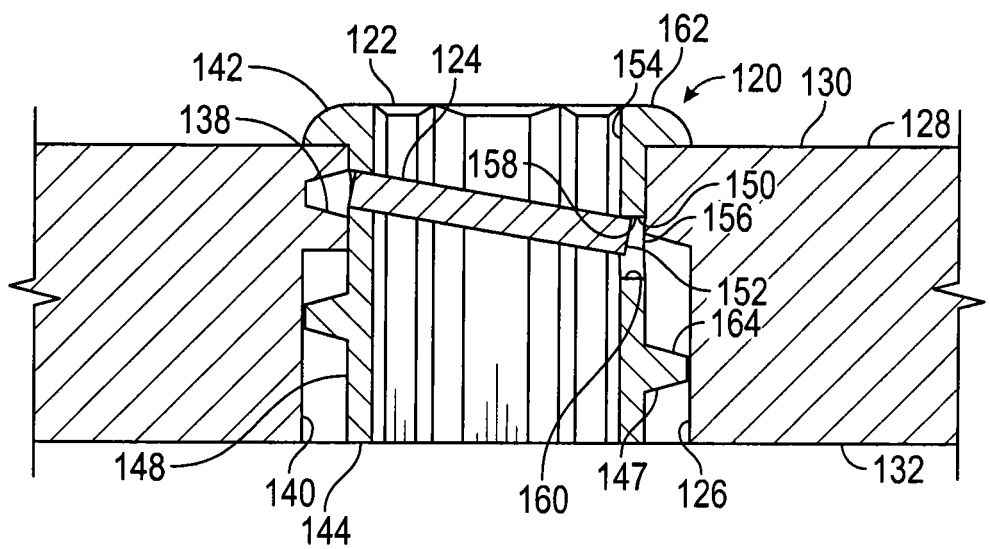
FIG. 13 is a sectional view taken along line 13-13 of FIG. 12.

FIGS. 11-13 illustrate another embodiment of a suture anchor insert 120 constructed in accordance with the inventive concepts disclosed herein. The suture anchor insert 120 has a body 122 and a crossbar 124. The body 122 is configured to be inserted into a hole 126 in a bone plate 128.

The bone plate 128 has an upper surface 130, a lower surface 132, a length 134, and a width 136. The plate 128 has a plurality of holes 126 formed therein extending through the plate 128 from the upper surface 130 to the lower surface 132. The plurality of holes 126 may comprise threaded holes, non-threaded holes, partially threaded holes, tapered holes, and straight holes, for example. As shown in FIG. 13, one or more of the plurality of holes 126 are threaded holes, having a threaded portion 138 extending from the upper surface 130 toward the lower surface 132 and ending medially between the upper surface 130 and the lower surface 132, and an open portion 140 extending from the ending of the threaded portion 138 medially between the upper surface 130 and the lower surface 132 and toward the lower surface 132.

The body 122 is configured to be slidably inserted into one of the holes 126 of the bone plate 128. The body 122 has a proximal end 142, a distal end 144, a length 146 extending between the proximal end 142 and the distal end 144 substantially corresponding to a thickness of the plate 128, and a sidewall 148 extending between the proximal end 142 and the distal end 144. The sidewall 148 is provided with plate engaging members 147 extending outwardly therefrom, and a transverse edge 150. The sidewall 148 defines a recess 154 within the body 122 of the suture anchor insert 120.

The crossbar 124 extends inwardly from the sidewall 148 across the recess 154 such that a free end 152 of the crossbar 124 is normally disposed distally of the transverse edge 150. The crossbar 124 is flexible such that when a distally directed force is applied to the crossbar 124, the free end 152 of the crossbar 124 is positioned in the recess 154 and when a proximally directed force is applied to the crossbar 124, the free end 152 of the crossbar 124 engages with the transverse edge 150 to limit proximal motion of the crossbar 124.

The sidewall 148 may be provided with a crossbar window 156 which is in communication with the recess 154. The crossbar window 156 has a proximal side 158 and a distal side 160 where the proximal side 158 of the crossbar window 156 defines the transverse edge 150. The crossbar 124 extends across the recess 154 such that the free end 152 of the crossbar 124 is normally disposed in the crossbar window 156.

In one embodiment, the plate engaging members 147 are in the form of a lip 162 extending outwardly at the proximal end 142 of the sidewall 148 and a helical thread 164. The proximal end 142 of the suture anchor insert 120 is configured to engage a driver to rotatably insert the suture anchor insert 120 into the plate 128. The suture anchor insert 120 is slidably inserted into the plate 128 by positioning the suture anchor insert 120 as the entrance of the hole 126. Thus positioned, a driver engages the suture anchor insert 120 at the proximal end 142 and the suture anchor insert 120 is slidably inserted into the hole 126 by applying a torsional force to the driver, causing the helical thread 164 of the suture anchor insert 120 to engage a threaded portion 166 of the hole 126. The suture anchor insert 120 is thus slidably inserted into the hole 126 such that the helical thread 164 is slidably inserted past the threaded portion 166 of the hole 126. Once the helical thread 164 passes through the threaded portion 138 of the hole 126 and into the open portion 140 of the hole 126, the suture anchor insert 120 is freely rotatable in the hole 126 of the plate 128.

One or more sutures may be attached to the suture anchor insert 120, as discussed above, by disposing the one or more sutures about the crossbar 124. The one or more sutures may be attached to suture anchor insert 120 in any suitable fashion, such as by using a suture threader, as discussed above.

The suture anchor insert 120 may be placed in differing locations on the plate 128 by slidably inserting the suture anchor insert 120 into one of the plurality of holes 126. The plurality of positions available for insertion of the suture anchor insert 120 enable placement of one or more sutures according to the needs of the surgeon at the time of the sutures. Maintaining the variability of the suture anchor insert 120, the suture anchor insert 120 may be provided as a kit including the plate 128 and at least one suture anchor insert 120.

Connecting a suture to a bone plate 12 is accomplished as follows. First a bone and soft tissue in need of repair are accessed using any suitable instrument, such as a scalpel, forceps, retractor, or combinations thereof. The plate 12 is secured to a bone using any suitable method, such as bone screws installed through one or more of the plurality of holes 16. At least one suture anchor insert 10 is slidably inserted into one of the holes 16 in the plate 12. At least one suture is disposed about the crossbar 40 of the suture anchor insert 10.

In the case of the embodiment of suture anchor insert 10, the suture anchor insert 10 is inserted prior to securing the plate 12 to the bone enabling the distal end 28 of the suture anchor insert 10 to be deformed to form the second lip 52, engaging the lower surface 20 of the plate 12. The embodiments of suture anchor insert 60 and suture anchor insert 120 may be inserted into the plate 12 and plate 128, respectively, prior or subsequent to securing the plate 12 and plate 128, respectively, to the bone.

If desired, the one or more sutures 54 may be attached to the suture anchor insert 10 prior to insertion into the plate. Otherwise, the configuration of the suture anchor insert 10 enables the one or more sutures 54 to be attached to the suture anchor insert 10 after the suture anchor insert 10 has been inserted in the plate 12, prior or subsequent to the plate 12 being secured to the bone. The sutures 54 may be attached to the suture anchor insert 10 in any suitable fashion. By way of example, the sutures 54 may be positioned about the crossbar 40 with a suture threader, as previously described.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or defined in the appended claims.

What is claimed is:

1. A suture anchor insert, comprising:
a body configured to be slidably inserted into a hole in a bone plate, the body having a proximal end, a distal end, a length extending between the proximal end and the distal end and so dimensioned as to substantially correspond to a thickness of the bone plate, a sidewall, a recess defined by the sidewall, and a transverse edge formed on the sidewall, the proximal end of the body terminating in at least one lip extending outwardly from the sidewall to be engageable with an upper surface of the bone plate to secure the body to the bone plate; and
a crossbar extending inwardly from the sidewall across the recess such that a free end of the crossbar is normally disposed distally of the transverse edge of the body, the crossbar being flexible such that when a distally directed force is applied to the crossbar, the free end of the crossbar is positionable in the recess and when a proximally directed force is applied to the crossbar, the free end of the crossbar is engageable with the transverse edge to limit proximal motion of the crossbar,
wherein the body has at least one slot formed within the sidewall and wherein the distal end of the body terminates in a second lip extending outwardly from the sidewall to be engageable with a lower surface of the bone plate.

2. The suture anchor insert of claim 1, wherein the slot extends from the distal end toward the proximal end.

3. The suture anchor insert of claim 2, wherein the body has a pair of diametrically opposed slots, each slot extending from the distal end toward the proximal end.

4. The suture anchor insert of claim 1, wherein the body is moveable between a compressed position wherein the body is slidable into the hole of the bone plate, and an expanded position wherein the body is secured within the hole in the bone plate.

5. The suture anchor insert of claim 4, wherein the body has a crossbar window, the crossbar window having a proximal end forming the transverse edge of the body, and wherein the crossbar is normally disposed in the crossbar window such that when the body is in the compressed position, the crossbar is moveable within the crossbar window without limiting compression of the body.

6. The suture anchor insert of claim 1, wherein the second lip is curved to facilitate slidably inserting the body into the bone plate.

7. The suture anchor insert of claim 1, wherein the body has a helical thread extending outwardly from the sidewall between the proximal end and the distal end.

8. The suture anchor insert of claim 7, wherein the proximal end of the body is configured to engageably receive a driver.

\* \* \* \* \*